(12) United States Patent
Amiche

(10) Patent No.: US 6,221,326 B1
(45) Date of Patent: Apr. 24, 2001

(54) METHOD FOR PREPARING HOLLOW SILICA PARTICLES

(75) Inventor: Frédéric Amiche, Vaucresson (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/171,438

(22) PCT Filed: Apr. 22, 1997

(86) PCT No.: PCT/FR97/00722

§ 371 Date: Oct. 20, 1998

§ 102(e) Date: Oct. 20, 1998

(87) PCT Pub. No.: WO97/40105

PCT Pub. Date: Oct. 30, 1997

(30) Foreign Application Priority Data

Apr. 22, 1996 (FR) .................................................. 96 05136

(51) Int. Cl.[7] .............................. C09C 1/30; C01B 33/18
(52) U.S. Cl. ..................... 423/335; 423/339; 106/409; 106/482
(58) Field of Search ..................................... 423/335, 339; 106/409, 481, 482

(56) References Cited

U.S. PATENT DOCUMENTS

| | | | |
|---|---|---|---|
| H1447 | * 6/1995 | Linton . | |
| 2,885,366 | * 5/1959 | Iler . | |
| 2,913,419 | * 11/1959 | Alexander . | |
| 4,011,096 | * 3/1977 | Sandell | 423/335 |
| 5,024,826 | * 6/1991 | Linton | 423/335 |
| 5,354,548 | * 10/1994 | Araya et al. | 423/335 |
| 5,512,094 | * 4/1996 | Linton . | |
| 5,932,191 | * 8/1999 | Cheallier et al. | 423/335 |

\* cited by examiner

Primary Examiner—Ngoc-Yen Nguyen
(74) Attorney, Agent, or Firm—Jean-Louis Seugnet

(57) ABSTRACT

A method for preparing hollow particles comprising a dense silica shell, by precipitating active silica from an aqueous alkaline metal silicate on a core constituted in a material other than silica and by eliminating the material without destroying the silica shell. The particles are used as insulating materials; as hollow fillers for polymers, building materials, rubber, paper, paint; as absorbing agents; as toothpaste abrasives or additives; as support for the absorption and/or graining out active matter, the liberation of the active matter being effected by the destruction of the silica core by mechanical rupture or by dissolving the silica shell in a basic medium or by diffusion; as sun screening agents or sun screening agent supports or for the formulation of liquid matter in solid form.

20 Claims, No Drawings

METHOD FOR PREPARING HOLLOW SILICA PARTICLES

This application is an application under 35 U.S.C. Section 371 of International Application Number PCT/FR97/00722, filed Apr. 22, 1997.

The subject-matter of the present invention is a method for preparing hollow particles comprising a dense silica shell by precipitation of active silica from an aqueous alkali metal silicate solution on a core composed of a material other than silica and removal of the said material without destruction of the silica shell. The said particles can be used as insulating materials, as hollow fillers for polymers, building materials, rubber, paper or paint, as absorbing agents, as dentifrice abrasives or additives, as supports for the absorption and/or the release of active material, the release of the said active material being achieved by destruction of the silica shell by mechanical rupture or by dissolution in basic medium of the silica shell or by diffusion, as sun protection agents or sun protection agent support, or for the formulation in solid form of liquid materials.

It is known to prepare heterogeneous particles composed of a dense silica shell deposited on a core composed of a charge other than silica by slow precipitation of active silica on the said core from an aqueous alkali metal silicate solution with adjustment of the pH using an acid (U.S. Pat. No. 2,885,366). According to this document, the precipitation operation must be carried out in a medium of low ionic strength with a rate of addition of silicate below a certain parameter S (expressed as weight of silica to be added per hour with respect to the weight of core to be coated) defined by the following equation $$S = (A/200)2^n$$

n being equal to (T-90)/10

A representing the specific surface, expressed in $m^2/g$, of the support to be coated and T the temperature in °C., in order to avoid the formation of nuclei of dense particles of silica.

For this reason, the operation of precipitating the active silica is lengthy; thus, the deposition of the order of 20 parts by weight of silica on 100 parts by weight of calcium carbonate at a temperature of the order of 80 to 90° C. requires a precipitation reaction lasting between 3 and 5 hours.

When the core of the said silica particles thus obtained is composed of a compound which is sensitive to acids, hollow silica particles can then be obtained by removing the core by acid attack (U.S. Pat. No. 5,024,826).

The inventor has found a novel method which makes it possible to prepare hollow particles of dense silica by rapid precipitation of active silica on a core composed of a material other than silica, without the risk of formation of nuclei of silica particles, and then removing the said material without destruction of the dense active silica shell.

In a simplified way, "dense" is understood to mean a silica shell formed of a continuous layer composed of a silica lattice, in contrast to a layer composed of a porous assembly of individual silica particles.

The present invention thus consists of a method for preparing hollow particles comprising a dense silica shell by precipitation of active silica from an aqueous alkali metal M silicate solution, with an $SiO_2/Na_2O$ ratio of at least 2, preferably of the order of 2.5 to 4, with adjustment of the pH using an acidifying agent, on a support made of a material other than silica, separation of the silica slurry formed and drying of the silica suspension recovered, with removal of the support, the said method being characterized in that the operation of formation of silica slurry by precipitation is carried out according to the following stages:

a first stage consisting in employing an initial vessel heel with a pH of the order of 8 to 10, comprising water at least one organic or inorganic support other than silica, which support is insoluble in water under the pH and temperature conditions of the slurry formation operation but which is capable of being at least partially removable without dissolution or destruction of the silica shell during the subsequent removal operation, an electrolyte salt from the group of alkali metals, the amount of electrolyte present being at least approximately 0.4 mol, preferably of the order of 0.4 to 1.5 mol, of alkali metal ion per liter of vessel heel, optionally a buffer or basic agent, at a temperature of the order of 80 to 98° C.;

a second stage consisting in introducing, into the said vessel heel, the alkali metal silicate in the form of an aqueous solution comprising at least approximately 100 grams of $SiO_2$/liter, preferably of the order of 100 to 330 grams of $SiO_2$/liter, and the acidifying agent, under conditions such that the kinetics K of formation of active silica, expressed in grams of silica/hour/gram of support, corresponds to a value $$K \geq 3(A/200)2^n, \text{ preferably } K \geq 4(A/200)2^n \text{ and very particularly } K \geq 6(A/200)2^n$$

n being equal to (T-90)/10

A representing the specific surface, expressed in $m^2/g$, of the support to be coated and T the temperature in °C., the reaction mixture exhibiting a substantially constant pH of the order of 8 to 10 and being maintained at a temperature of the order of 80 to 98° C., until the desired amount of silica has been formed, and in that particles obtained comprising an active silica shell and a core composed of the said support are subjected to an operation for the removal of the material constituting the support, without dissolution or destruction of the active silica shell.

The choice of the silicate and the acidifying agent for implementing the method of the invention is carried out in a way well known per se. The alkali metal silicate is advantageously a sodium or potassium silicate. Mention may very particularly be made of sodium silicate.

Use is generally made, as acidifying agent in the second stage of slurry formation, of an inorganic acid, such as sulphuric acid, nitric acid or hydrochloric acid, or an organic acid, such as acetic acid, formic acid or carbonic acid. It is preferably sulphuric acid. The latter can be employed in the dilute or concentrated form, preferably in the form of an aqueous solution exhibiting a concentration of the order of 60 to 400 g/l. Carbonic acid is preferably employed in the gaseous form.

Mention may be made, among materials which can be employed as support in implementing the method of the invention, of any inorganic or organic, solid or liquid compound which is inert with respect to active silica (hydroxylated silica), which is insoluble in water under the pH and temperature conditions of the slurry formation operation, which has any shape (spherical, acicular, and the like), and which is capable of being removed from the particles containing it by a treatment which depends on its chemical and physical nature.

The said support is preferably in solid form. "Compound which is inert with respect to silica" is understood to mean any compound which remains stable under the conditions for precipitation of silica. "Compound which is insoluble in water" is understood to mean any compound exhibiting a solubility in water of less than approximately 0.5% by weight at 25° C.

As regards the operation of removing the material constituting the support (core), this can be, according to the nature of the said material, a treatment by dissolution (using an acid or a non-polar solvent) for solids, followed by a separation operation; a heat treatment, whatever the material; or a simple separation operation, when it is a liquid. Whatever the nature of the material (solid, liquid, organic or inorganic), the latter can be removable by heat treatment at a temperature which is at least equal to that of vaporization or of decomposition of the said material, but which does not damage the silica shell. The solid materials which can be employed include those which can be removed by dissolution using an inorganic or organic acid at a pH of less than 8, preferably of the order of 2 to 7, or using a non-polar solvent, this dissolution operation being followed by separation, for example by centrifuging, filtration, distillation, evaporation, dialysis, osmosis, and the like. Mention may be made, among solid materials capable of being removed by dissolution using an acid, preferably in aqueous solution, of inorganic salts, such as calcium carbonate, barium carbonate, and the like, metals, such as copper and the like, acid-soluble organic polymers, such as amine-comprising polymers (such as those derived from vinylpyridine), crosslinked polysaccharides, and the like. The nature of the acid to be employed is, of course, a function of the chemical nature of the said material.

Mention may be made, among solid materials capable of being dissolved by non-polar solvents, of non-alkalisoluble organic polymers, such as, in particular, polystyrenes, polyacrylic esters, polymethacrylic esters, polyethylenes, polyamides, polyesters, and the like. The nature of the non-polar solvent to be employed is, of course, a function of the chemical nature of the said material. Chlorinated solvents (dichloromethane, and the like), tetrahydrofuran, and the like, are generally well suited.

As regards the liquid materials, use can be made of those which can be removed by a simple separation operation, such as centrifuging, filtration, distillation, evaporation, dialysis, osmosis, and the like.

Mention may be made, among the materials capable of thus being separated, of vegetable oils, mineral oils, liquid petrolatum, silicone oils, and the like.

The support employed can be of any size according to the desired empty volume, for example of the order of 20 nm to 30 $\mu$m, preferably of the order of 50 nm to 20 $\mu$m.

Mention may in particular be made, among the electrolytes which can be employed to prepare the vessel heel, of the salt of the starting silicate metal and of the acidifying agent; it is preferably sodium sulphate; however, sodium chloride, nitrate or hydrogencarbonate may be preferred if the presence of residual sulphate ions is not desired.

The first stage of the slurry formation operation consists in preparing the initial vessel heel.

If the support employed is a solid material, the latter can be introduced as is or, preferably, in the form of an aqueous dispersion. If it is a liquid, the latter is preferably introduced in the form of an aqueous emulsion.

The amount of support which can be employed is such that the vessel heel formed contains of the order of at least 10% of its weight of solid support or of the order of at least 10% of its volume of liquid support; the said vessel heel can generally contain up to 50% of its weight or of its volume of solid or liquid support.

A buffer or basic agent can be employed in the initial vessel heel in order to ensure a pH of the said vessel heel of the order of 8 to 10.

Mention may be made, as buffer or basic agent, of alkali metal hydroxides., such as sodium hydroxide, dissolved alkali metal silicates, alkali metal phosphates, alkali metal hydrogencarbonates, and the like.

The vessel heel obtained is brought to a temperature of the order of 80 to 98° C.

The second stage of the operation of slurry formation by precipitation consists in adding the silicate solution and the acidifying agent simultaneously to the vessel heel, which is kept stirred.

The respective amounts of alkali metal silicate and of acidifying agent are chosen so as to obtain the abovementioned kinetics K of formation of active silica and so as to maintain the pH of the reaction mixture at a substantially constant value of the order of 8 to 10 throughout the introduction of the two reactants. These two reactants are introduced while maintaining the mixture at a temperature of the order of 80 to 98° C.

The introduction of the silicate solution is halted when the desired amount of silica has been formed. The minimum desired amount of silica is that corresponding to a deposition of the order of 1 to 150 parts by weight of $SiO_2$ per 100 parts by weight of support.

This second stage generally lasts of the order of 30 minutes to 2 hours.

The pH of the mixture obtained at the end of the second stage, after halting the introduction of the reactants, is subsequently brought, if necessary, to a value of less than 7, preferably of the order of 4 to 5.

The mixture obtained at the end of the second stage, after halting the introduction of the reactants, is optionally allowed to mature for approximately 10 to 30 minutes under the same temperature conditions. This optional maturing operation can be carried out either before or after having brought the pH of the mixture to a value of less than 7, preferably of the order of 4 to 5, if this pH correction is necessary.

On conclusion of the abovedescribed slurry formation operations, a silica slurry is obtained which is subsequently separated (liquid/solid separation); this operation generally consists of a filtration (for example separation by settling, use of a rotary vacuum filter), followed by washing with water and optionally with alcohol and with ether.

The silica suspension thus recovered (filtration cake) is subsequently dried (oven, kiln, atomization, vacuum).

The particles thus obtained can exhibit a silica shell thickness of the order of 2 to 200 nm, preferably of the order of 2 to 50 nm, for a support core size of the order of 20 nm to 30 $\mu$m, preferably of the order of 50 nm to 20 $\mu$m.

As mentioned above, the operation of removing the material constituting the support can be carried out by various types of treatment: heat treatment, whatever the nature of the support, dissolution, followed by separation, if it is a solid, or simple separation, if it is a liquid.

When it is a heat treatment, the heat treatment is carried out at a temperature at least equal to that necessary to vaporize or calcine the material constituting the support; it can be carried out on the particles obtained after washing the filtration cake or on the dried particles.

When it is a treatment by acid dissolution, the treatment is carried out at a pH of less than 8, preferably of the order of 2 to 7, before or after separation of the slurry of particles comprising a silica shell.

Thus, the said treatment can be carried out equally well:

at the end of the second stage of the slurry formation operation, on the slurry obtained after halting the introduction of the reactants and optional maturing of the reaction mixture or at the end of the second stage of the operation of slurry formation by precipitation, during the maturing of the reaction mixture or after separation of the slurry, on the filtration cake, before or after washing or after drying the particles and redispersion of the said particles in water.

The acids which can be employed in carrying out the acidic chemical treatment are chosen from those capable of dissolving the material constituting the core.

Thus, when it is calcium carbonate, the acids preferably employed are strong acids, in particular hydrochloric and nitric acids, in the form of aqueous solutions.

The addition of acid is preferably carried out gradually, until the pH stabilizes at a value of less than 8, preferably of the order of 2 to 4.

The treated particles are subsequently recovered by centrifuging, filtration, distillation, evaporation, dialysis, osmosis, and the like, washed with water and dried.

When it is a dissolution treatment with a non-polar solvent, the treatment is carried out after drying the particles, redispersion of the said particles in the said solvent and then separating by centrifuging, filtration, distillation, evaporation, dialysis, osmosis, and the like, washing with water and drying.

According to an alternative embodiment of the invention, the silica shell additionally contains traces of polyvalent cations, such as $Mg^{2+}$, $Ca^{2+}$, $Ba^{2+}$ or $Pb^{2+}$, preferably introduced in the aqueous solution form either during the slurry formation operation in the first stage, in the vessel heel, or in the second stage, during the simultaneous addition of reactants. This presence of cations is very particularly advantageous for introducing microporosity into the dense silica shell, by acidic attack in order to remove the core.

The method which forms the subject-matter of the invention is well suited to the preparation of hollow particles of dense silica, which in addition is optionally microporous, exhibiting:

a BET surface of the order of 15 to 800 $m^2/g$ a DOP oil uptake of greater than 500 ml/100 g of silica and a shell thickness of the order of 2 to 200 nm, preferably of the order of 2 to 50 nm.

The said particles exhibit a particle size which is a function of the size of the starting support; the latter can preferably be of the order of more than 20 nm to 30 $\mu m$, preferably of the order of 50 nm to 20 $\mu m$.

The BET specific surface is determined according to the Brunauer-Emmet-Teller method described in "The Journal of the American Chemical Society", Vol. 60, page 309, February 1938, which corresponds to NFT Standard 45007 (November 1987).

The DOP oil uptake is determined according to ISO Standard 787/5 employing dioctyl phthalate.

The thickness of the shell is determined by electron microscopy.

The hollow particles obtained according to the method of the invention can be used as thermal or sound insulating material or constituent thereof as hollow fillers for polymers, building materials, rubber, paper (ink jet paper), paint, and the like as absorbing agent (effluent treatment, absorbent paper, and the like)

as dentrifice abrasive as support for the absorption and/or for the controlled release of active materials which can be introduced onto the support as is in the liquid state, or in the liquid form in solution or in the molten state, the release of the active material then being achieved by destruction of the silica shell, for example by dissolution in a highly basic medium or by mechanical action or by diffusion.

Thus, they can be used for the absorption of setting accelerating agents or viscosifying agents for concretes and building materials, with controlled release of the active principle of oxidizing agents which can be used in formation fracturing operations in the petroleum field and the controlled release of pharmaceutical, agrochemical, food, cosmetic, flavoring or perfumery active principles of bactericides for the cleaning of hard surfaces in household or industrial detergency of softening or moisturizing agents for body hygiene of enzyme (application in household detergency)

as sun protection agent or as sun protection agent support (anti-UV)

as dentrifice additive or abrasive with controlled release of absorbed flavorings or therapeutic active principles (fluorinated derivatives, bactericides, and the like); when the active material is a flavoring, the active material, thus placed on a support, can have a limited reactivity and/or adsorption with and/or on conventional abrasives generally exhibiting high specific surfaces for the formulation in solid form of products conventionally used in liquid formulations, products such as biologically active liquid materials for plant-protection or therapeutic application, such as organic, mineral, vegetable or silicone oils or derivatives thereof, for the formulation of solids, such as soaps.

A second subject-matter of the invention consists of hollow dense silica particles exhibiting a BET surface of the order of 15 to 800 $m^2/g$ a DOP oil uptake of greater than 500 ml/100 g of silica a shell thickness of the order of 2 to less than 10 nm.

They can exhibit a particle size of greater than approximately 1 $\mu m$, preferably of greater than approximately 10 $\mu m$, very particularly of greater than approximately 15 $\mu m$.

The particles exhibiting a low shell thickness of less than approximately 20 nm, preferably of less than approximately 10 nm, are easily broken (in particular if they exhibit a particle size of greater than approximately 1 $\mu m$, preferably of greater than approximately 10 $\mu m$, very particularly of greater than approximately 15 $\mu m$); they can be used as support for active materials for the protection and/or the release of active materials, such as flavorings, flavoring derivatives, fragrances, emollients, humectants, moisturizing agents, conditioning agents, and the like, the release of the active material being achieved by mechanical rupture of the silica shell by simple mechanical stress (crushing by passing into an atomizer, crushing by manual spreading over the skin, and the like).

The said active materials can be absorbed by simply bringing into contact in liquid form [either as is or molten (when they are solids, waxes or gels) or in solution or dispersion in a vehicle] with the said brittle hollow particles of dense silica.

The following examples are given by way of illustration.

EXAMPLE 1

Preparation of Particles Composed of a Calcium Carbonate Core and of a Silica Shell A vessel heel is prepared by introduction, into a 15 liter reactor, of 5 liters of water, of 0.68 mol/liter of vessel heel of sodium in the form of sodium chloride, of 1150 g of precipitated calcium carbonate exhibiting a particle size of 4 μm and a BET specific surface of 16 m$^2$/g, and of sodium silicate, with an $SiO_2/Na_2O$ ratio of 3.5 (aqueous solution comprising 130 g of $SiO_2$ per liter), in an amount corresponding to a concentration of 3 g of $SiO_2$ per liter of vessel heel. The vessel heel, with a pH of 9, is brought to 90° C. and kept stirred.

The following are subsequently introduced simultaneously an aqueous sodium silicate solution with an $SiO_2/Na_2O$ ratio of 3.5, the concentration of which is 130 g of $SiO_2$ per liter of solution, and an aqueous sulphuric acid solution comprising 80 g of acid per liter, so as to form 230 g of silica in 30 minutes.

After maturing for 30 minutes, the slurry obtained is filtered; the filtration cake is washed with water and then dried in an oven at 80° C.

Analysis of the product by electron microscopy (TEM) shows that the thickness of the silica layer deposited is of the order of 5 nm.

The BET surface of the particles is 21 m$^2$/g. The kinetics of addition of the sodium silicate was 0.4 g ($Sio_2$)/h/g ($CaCO_3$), against 0.08 g ($SiO_2$)/h/g ($CaCO_3$) according to the prior art (U.S. Pat. No. 2,885,366).

Removal of the Core 300 g of the dry particles obtained above are redispersed in 2.7 liters of water. Concentrated hydrochloric acid (8.5M) is added so as to bring the pH down to 2; the addition of acid is continued for 30 minutes until this pH has stabilized.

The product obtained is subsequently filtered, washed copiously and dried in an oven at 80° C.

The hollow particles obtained exhibit the following characteristics:

a BET surface of 207 m$^2$/g a DOP oil uptake of 612 ml/100 g of silica a shell thickness of the order of 5 nm.

EXAMPLE 2

50 g of hollow silica prepared in Example 1 are dispersed, with gentle shearing, in 500 ml of cyclomethicone (volatile silicone oil Mirasil CM4 sold by Rhône-Poulenc).

The mixture is left under gentle shearing at room temperature for 10 minutes. The amount of cyclomethicone absorbed is measured by the increase in the weight of the dry particles obtained. It is found that the silica absorbs 5 times its weight of silicone oil.

EXAMPLE 3

50 g of hollow silica prepared in Example 1 are dispersed, with gentle shearing, in 500 ml of mint flavoring Herbal.

The mixture is left under gentle shearing at room temperature for 10 minutes. The amount of flavoring absorbed is measured by the increase in the weight of the dry particles obtained. It is found that the silica absorbs 5 times its weight of flavoring.

EXAMPLE 4

50 g of hollow silica prepared in Example 1 are dispersed, with gentle shearing, in 500 ml of a 15% solution of perfume concentrate in cyclomethicone. The mixture is left with gentle shearing at room temperature for 10 minutes. The amount of perfume concentrate solution absorbed is measured by the increase in the weight of the dry particles obtained. It is found that the silica absorbs 5 times its weight of perfume concentrate.

EXAMPLE 5

Preparation of Particles Composed of a Calcium Carbonate Core and of a Silica Shell A vessel heel is prepared by introduction, into a 15 liter reactor, of 5 liters of an aqueous dispersion comprising 230 g/l of precipitated calcium carbonate exhibiting a diameter of 17 μm and a BET specific surface of 4 m$^2$/g, of sodium sulphate in an amount corresponding to 0.43 mol of sodium per liter of vessel heel, and of 124 g of aqueous sodium silicate solution, comprising 130 g of $SiO_2$ per liter, with an $SiO_2/Na_2O$ ratio of 3.5, in order to obtain a pH of 9 for the vessel heel.

The vessel heel is brought to 90° C. and kept stirred. The following are subsequently introduced simultaneously an aqueous sodium silicate solution with an $SiO_2/Na_2O$ ratio of 3.5, the concentration of which is 130 g of $SiO_2$ per liter of solution, and gaseous $CO_2$, so as to form 57.5 g of silica in 45 minutes.

After maturing for 30 minutes, the slurry obtained is filtered; the filtration cake is washed with water and then dried in an oven at 80° C.

Analysis of the product by electron microscopy (TEM) shows that the thickness of the silica layer deposited is of the order of 5 nm.

The BET surface of the particles is 4.2 m$^2$/g. The kinetics of addition of the sodium silicate was 0.07 g ($SiO_2$)/h/g ($CaCO_3$), against 0.02 g ($SiO_2$)/h/g ($CaCO_3$) according to the prior art (U.S. Pat. No. 2,885,366).

Removal of the Core 300 g of the dry particles obtained above are redispersed in 2.7 liters of water.

Concentrated hydrochloric acid (8.5M) is added so as to bring the pH down to 2; the addition of acid is continued for 30 minutes until this pH has stabilized. The product obtained is subsequently filtered off, washed copiously with water, then with ethanol and finally with ether, and dried under vacuum.

The hollow particles obtained exhibit the following characteristics:

a BET surface of 198 m$^2$/g a DOP oil uptake of 1740 ml/100 g of silica a shell thickness of the order of 5 nm.

What is claimed is:

1. A process for the preparation of hollow particles comprising a dense silica shell, said process comprising the steps of
   1) precipitating active silica from an aqueous alkali metal M silicate solution, with an $SiO_2/M_2O$ ratio of at least 2, on a support made of a material other than silica to form a silica slurry;
   2) separating the formed silica particles from the silica slurry and drying the silica particles; and
   3) removing the support without dissolution or destruction of the active silica shell; wherein, in step 1), the formation of silica slurry is carried out according to the two following stages:

a first stage comprising forming an initial vessel heel with a pH of about 8 to about 10 by mixing:
   water
      at least one organic or inorganic support other than silica, said support is insoluble in water during step 1) and is at least partially removable without dissolution or destruction of the silica shell,
      an electrolyte alkali metal in an amount of at least about 0.4 mole of alkali metal ion per liter of vessel heel, and
      optionally a buffer or basic agent, at a temperature of about 80 to 98° C.; and
   a second stage comprising adding, into said vessel heel,
      the alkali metal silicate in the form of an aqueous solution comprising at least about 100 grams of $SiO_2$/liter, and
      an acidifying agent, in order to form a reaction mixture under conditions such that the kinetics K of formation of active silica, expressed in grams of silica/hour/gram of support, corresponds to a value $$K \geq 3(A/200)2^n$$

wherein n is equal to (T-90)/10
   A is the specific surface, expressed in $m^2/g$, of the support to be coated, and
   T is the temperature of the reaction mixture in ° C.,
   the reaction mixture exhibiting a substantially constant pH of about 8 to about 10 and being maintained at a temperature of about 80 to about 98° C., and
      wherein the particles obtained after step 2) comprise an active silica shell and a core composed of said support.

2. A process according to claim 1, wherein in step 1) M is sodium and the $SiO_2/Na_2O$ ratio is of about 2.5 to about 4, in the first stage the amount of electrolyte is of about 0.4 to 1.5 mole alkali metal ion per liter of vessel heel, in the second stage the alkali metal silicate solution comprises about 100 to about 330 grams of $SiO_2$/liter, and $K \geq 4(A/200)2^n$.

3. A process according to claim 2, wherein $K \geq 6(A/200)2^n$.

4. A process according to claim 1, wherein the alkali metal silicate is a sodium or potassium silicate.

5. A process according to claim 1, wherein the acidifying agent is an inorganic or organic acid.

6. A process according to claim 5, wherein the acidifying agent is sulphuric, nitric, hydrochloric, acetic, formic or carbonic acid.

7. A process according to claim 6, wherein the acidifying agent is sulphuric acid, in the form of an aqueous solution exhibiting a concentration of about 60 to about 400 g/l.

8. A process according to claim 1, wherein the material constituting the support is removed by heat treatment, dissolution using an inorganic or organic acid at a pH of less than 8, dissolution using a non-polar solvent when the support are solid materials, or separation of liquid when the support are liquid materials.

9. A process according to claim 8, wherein the solid support materials are inorganic salts, metals, organic polymers or crosslinked polysaccharides which are soluble at a pH of less than 8 and the solid support materials are removed by dissolution using an acid.

10. A process according to claim 9, wherein said solid support material is calcium carbonate.

11. A process according to claim 8, wherein the solid support materials are non-alkali-soluble organic polymers and the solid support materials are removed by dissolution using a non-polar solvent.

12. A process according to claim 8, wherein the liquid support materials are vegetable oils, mineral oils, liquid petrolatum, or silicone oils.

13. A process according to claim 12, wherein the separation is a centrifugation, filtration, distillation, evaporation, dialysis, or osmosis.

14. A process according to claim 1, wherein the material of the support other than silica exhibits a size of about 20 nm to about 30 µm.

15. A process according to claim 14, wherein the size is of about 50 nm to about 20 µm.

16. A process according to claim 1, wherein the electrolyte is sodium sulphate, sodium chloride, sodium nitrate or sodium hydrogencarbonate.

17. A process according to claim 8, wherein the support, when it is a solid material, is employed in the form of an aqueous dispersion or, when it is a liquid, in the form of an aqueous emulsion.

18. A process according to claim 1, wherein the amount of support is such that the vessel heel formed contains at least about 10% of its weight of solid support or of about at least 10% of its volume of support in liquid form.

19. A process according to claim 18, wherein the vessel heel contains up to 50% of its weight or of its volume of solid or liquid support.

20. A process according to claim 1, wherein, in the second stage, the formation of slurry is carried out by simultaneously adding the alkali metal silicate and the acidifying agent, until the formation of at least 1 to 150 parts by weight of $SiO_2$ per 100 parts by weight of support.

* * * * *